United States Patent [19]

Blake, III

[11] Patent Number: 4,506,669

[45] Date of Patent: Mar. 26, 1985

[54] SKIN APPROXIMATOR

[76] Inventor: Joseph W. Blake, III, 88 Main St., New Canaan, Conn. 06840

[21] Appl. No.: 421,563

[22] Filed: Sep. 22, 1982

[51] Int. Cl.³ .................. A61B 17/04; A61B 17/30; B25B 9/02

[52] U.S. Cl. .................. 128/334 R; 128/354; 128/335; 294/99.2

[58] Field of Search .......... 128/335, 354, 334 R, 128/346, 321; 81/43, 419, 92

[56] References Cited

U.S. PATENT DOCUMENTS

| 86,016 | 1/1869 | Howell | 128/321 |
|---|---|---|---|
| 721,480 | 2/1903 | van Schott | 81/43 |
| 2,237,589 | 6/1941 | Dole | |
| 2,594,102 | 4/1952 | Vollmer | |
| 3,378,010 | 4/1968 | Codling et al. | 128/346 |
| 3,604,425 | 9/1971 | LeRoy | 128/325 |
| 3,906,957 | 9/1975 | Weston | 128/354 |
| 4,162,678 | 7/1979 | Fedotov et al. | 128/334 R |

Primary Examiner—C. Fred Rosenbaum
Assistant Examiner—Gene B. Kartchner
Attorney, Agent, or Firm—Peter K. Kontler

[57] ABSTRACT

A skin approximator has two hinged together sections provided with free ends movable towards and away from each other. The free ends carry arms which are so hinged to them that they pivot during movement of the sections towards each other and when barbs provided on these arms are inserted into the skin at opposite sides of a wound. This pivoting movement causes skin edge portions extending along the wound to become everted before they move into abutment with one another.

17 Claims, 7 Drawing Figures

SKIN APPROXIMATOR

BACKGROUND OF THE INVENTION

The present invention relates to a medical device in general, and more particularly to a device used in surgical applications.

Still more specifically, the invention relates to a skin approximator.

Devices of this general type are known per se. Their purpose is to draw the skin edges together from opposite sides of a wound, to permit the wound to be closed by suturing or stapling. A problem with the prior art devices is that they are only capable of butting the skin edges together. It is known, however, that this does not produce as neat a final scar as is obtained when the skin edges are everted, i.e. bent outwardly (relative to the skin surface) so that they in effect form a slight "bead". This leaves the person closing the wound with the choice of simply butting the skin edges with the aid of the approximator, leaving the patient to accept the less attractive scar tissue development which results from this, or to attempt to evert the skin edges by hand which is difficult if not impossible to accomplish.

OBJECTS AND SUMMARY OF THE INVENTION

Accordingly, it is a general object of the present invention to overcome the disadvantages of the prior art.

A more particular object of the invention is to provide an improved skin approximator which is not possessed of the prior art drawbacks.

Still a more specific object of the invention is to provide such an improved skin approximator which is capable of everting the skin edges as it draws them together in preparation for closing of the wound.

Another object of the invention is to provide such an improved skin approximator which is uncomplicated and therefore simple and inexpensive to produce.

A still further object is to provide a skin approximator which can be produced as a onetime (i.e. throwaway) device or as a reusable (i.e. autoclavable) device.

A concomitant object of the invention is to provide a skin approximator which is simple to use and reliable in service.

Pursuant to the above objects, and still others which will become apparent hereafter, one aspect of the invention resides in the provision of a medical device, particularly a skin approximator. Briefly stated, such a device may include first means for engaging the skin at opposite sides of a wound, second means for drawing the skin together across the wound so as to close the same, and third means for everting the edges of the skin before they move into a position of mutual abutment in response to operation of the second means.

The approximator according to the invention may, as mentioned earlier, be made as a one-time device, i.e. a device which is used one time only and discarded. If so, it is advantageously made at least predominantly of synthetic plastic material, for example polypropylene, ABS, polycarbonate, nylon, acetal or polysulfone which is autoclavable, and may e.g. be produced by known per-se injection molding techniques. Such a device may be supplied to the user in a sealed sterile package which is opened immediately prior to use to retain its sterility.

The approximator may, however, also be made as a reusable device, which is autoclavable in order to restore sterility between uses. In that event the device may advantageously be wholly or predominantly of stainless steel, although other metals such as e.g. nickel or chrome or even synthetic plastic materials such as polysulfone (by themselves or in combination with one another and/or with stainless steel) may also be used.

The novel features which are considered to be characteristic of the invention are set forth in particular in the hereto appended claims. The improved device itself, however, together with details of its construction and the best mode of operation currently known to applicant, as well as additional features and advantages of the invention, will be best understood upon a perusal of the following detailed description of specific although purely exemplary embodiments with reference to the accompanying drawing.

BRIEF DESCRIPTION OF THE DRAWING

FIG. 2 is a view similar to FIG. 1, but showing the device in the end position in which the skin edges are drawn together and everted in readiness for closing of the wound by stapling, suturing or the like;

DESCRIPTION OF PREFERRED EMBODIMENTS

Figure 1:
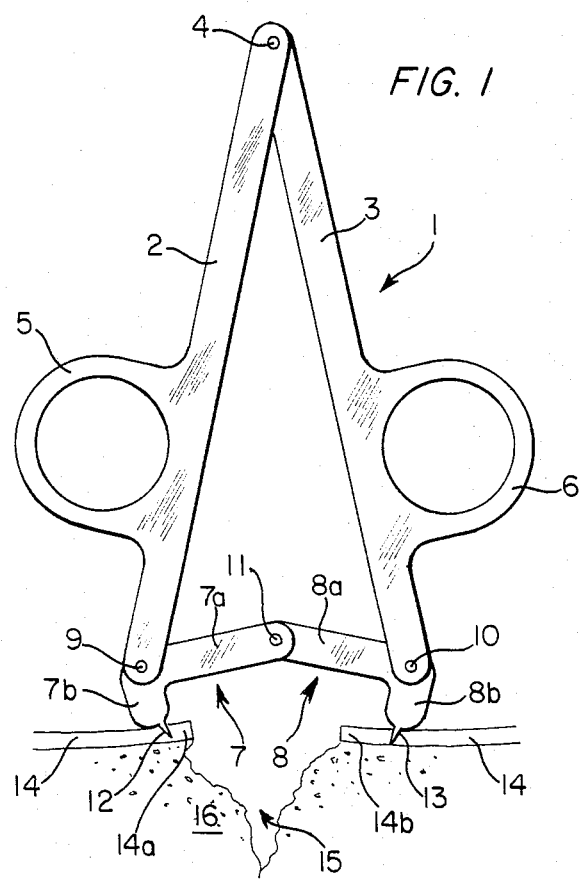
FIG. 1 is an elevational view of an embodiment of the inventive device, shown on a wound and with the device in its initial or starting position.
Figure 3:
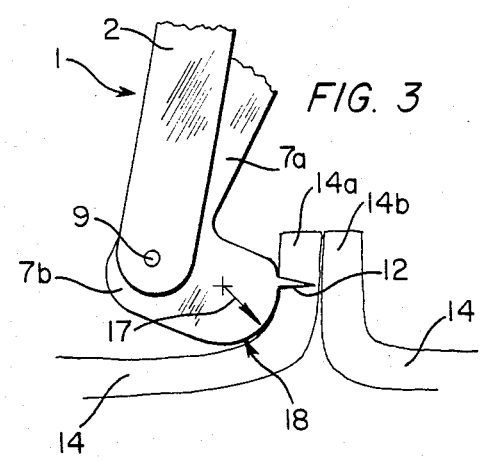
FIG. 3 is a detail view of FIG. 2 on an enlarged scale.
Figure 2:
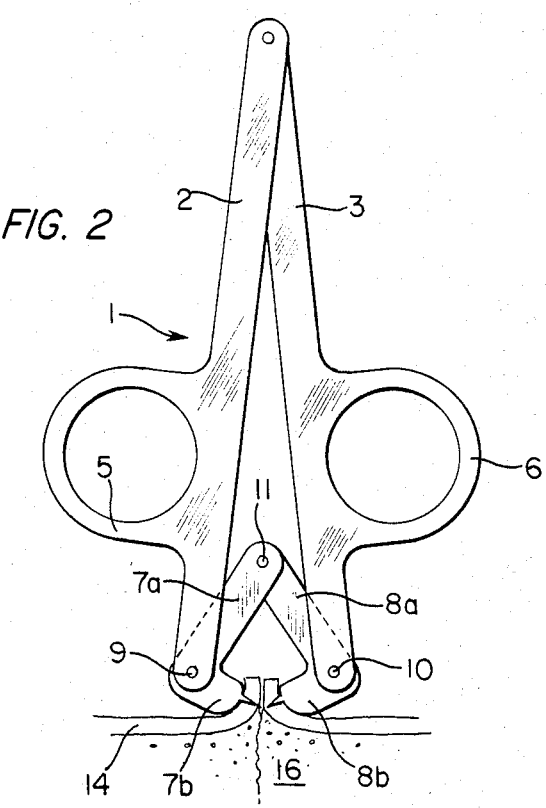

Referring now to the drawing in detail, and firstly to FIGS. 1-3 thereof, it will be seen that these Figures illustrate one embodiment of the inventive device 1.

In this embodiment the device has two sections 2 and 3 which are hinged or pivoted together at or near one end at the location 4 about which they can turn or pivot, in order for their opposite (lower) ends to move towards and away from one another. The location 4 could, of course, be positioned elsewhere than illustrated. Sections 2 and 3 are each provided with a finger loop 5 and 6, respectively, into which fingers of a user may be placed. The loops 5 and 6 are optional: they could be omitted as long as adequate engagement of the fingers with the sections 2 and 3 is otherwise assured, e.g. by providing the outwardly directed surfaces of the sections 2, 3 with sufficiently large finger-contact surface portions which may be smooth, rough or be provided with finger-receiving depressions.

Mounted on the lower end portions of the sections 2,3 are respective arms 7 and 8. These are basically L-shaped, each having a longer part 7a, 8a and a shorter part 7b, 8b, respectively. At or near the junction of its longer and shorter parts each arm 7, 8 is pivoted by pivots 9 and 10 to one of the sections 2 and 3. In addition, the free proximal ends of the longer parts 7a, 8a are pivoted to each other at 11.

Each of the shorter parts 7b, 8b is provided at its free end (i.e. the one distal from the respectively associated longer part) with at least one (but usually two or more) barb or skin-penetrating needle point 12, 13. Depending upon the material from which the arms 7, 8 are made, the barbs 12, 13 may be unitary with the respective arms (if the arms are of metal, for example) or they may be separate components embedded or otherwise anchored in or to the arms (for example, they might be partially embedded steel pins if the arms are of synthetic plastic material; in that event, the pins may simply be molded in place during manufacture of the arms 7, 8).

FIGS. 1 and 2 show the device in its starting and end positions, respectively. In FIG. 1 the device 1 is seen with its barbs 12, 13 penetrating into the marginal portions of the skin 14 at the opposite sides of a wound 15. The tissue underlying the skin 14 is shown diagrammatically and designated with reference numeral 16.

When pressure is exerted upon the sections 2 and 3 in a sense moving them towards one another, the barbs 12, 13 inserted into the skin 14 will pull the skin across the wound 15. This is the action which is already known from prior-art skin approximators.

However, according to the present invention this pulling movement is not intended to terminate in flat abutment of the skin edges, as in the prior art. Instead, the invention intends to—and does—achieve everting of the skin edge portions 14a and 14b. "Everting" is defined as folding of the skin edge portions 14a and 14b in direction outwardly of the wound 15, so as to form a skin ridge.

This is accomplished in the inventive device due to the L-shaped configuration of the arms 7, 8, their pivotal mounting at 9, 10 and 11, and the fact that the end faces of the free ends of the shorter parts 7b, 8b (where the barbs 12, 13 project) are curved rather than flat. As a result of these factors pivoting of the sections 2, 3 towards each other about the axis defined by pivot 4, causes pivoting of the arms 7, 8 about 9, 10, 11 from the position of FIG. 1 to the position of FIG. 2. During this movement the end faces of the parts 7b, 8b curl or roll on the surface of skin 14; since at the same time the free ends of parts 7b, 8b are moving towards one another (and pulling the skin 14 across wound 15), the result is an eversion of the skin edge portions 14a, 14b to the position shown in FIG. 2, in which the edge portions project outwardly from the wound 15 and abut with one another only after they have assumed this orientation (FIG. 2). As mentioned before, the scar which will develop on healing of a wound which has been closed by suturing, stapling or the like with the skin edge portions everted as in FIG. 2, will be much less noticeable (and hence less objectionable) than those obtained by edge-to-edge abutment as in the prior art.

FIG. 3 shows that the radius of curvature 17 or the respective edge face 18 (only one shown if FIG. 3) is advantageously located outside of (i.e. eccentric with reference to) the center of the barb or barbs (barb 12 shown in FIG. 3). This is not absolutely necessary for the inventive device to operate in the intended manner, but it does aid in the eversion of the skin and is therefore currently preferred.

Figure 4:
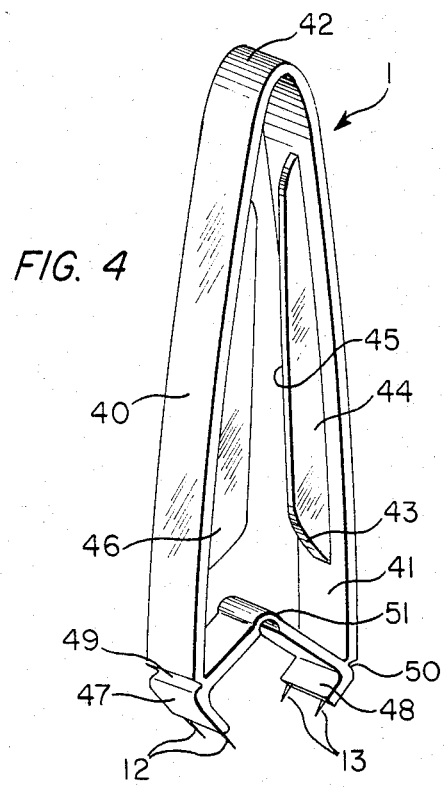
FIG. 4 is a perspective view illustrating another embodiment of the inventive device.

FIG. 4 shows an embodiment of the inventive device which is especially simple and particularly well suited to be made from synthetic plastic material by molding, for example by injection molding.

The device in toto is again identified with reference numeral 1. It has two sections 40, 41 which at the top region 42 are unitary with one another; in other words, the sections 40, 41 are molded so as to be of one piece with one another, with the region 42 serving as a hinge about which they can be springily moved towards and away from each other. The inner side of one of the arms (here 41) may be formed with a slot or recess 43 which in FIG. 4 is defined between two projecting blades or ribs 44, 45; the inner side of the other arm (here 40) is then provided with a projection 46 (here blade or rib-shaped) which enters slot 43 when sections 40, 41 move towards one another. This arrangement improves the guidance of the sections during their respective movement and also defines the end position assumable by these sections. However, the elements 43–46 can be omitted without detracting from the basic intended function according to the invention.

The free ends of sections 40, 41 carry respective L-shaped arms 47 and 48 whose endfaces on their shorter sections are again provided with barbs 12, 13 as described before. The endfaces themselves are curved as in FIG. 2 or in FIG. 3 although this is not visible in FIG. 4 due to the angle of view shown there. Arms 47 and 48 are unitary (molded of one piece) with the sections 40 and 41, respectively; they are also unitary with one another. Where the arms join the sections 40 and 41 the device 1 is molded with weakened portions or zones 49, 50 consitituting integral hinges about which the arms 47, 48 can swing or pivot relative to the sections 40, 41. A similar weakened portion or zone 51 is molded at the junction of the arms 51.

The operation of the device in FIG. 4 is similar to that of the device in FIGS. 1–3 and therefore is not believed to require further explanation. It is clear that the device in FIG. 4 is especially well suited to be made of one piece (unitary) by molding (e.g. injection molding) from suitable synthetic plastic material. The barbs 12, 13 can be molded in place during manufacture of the device or if desired, they can be inserted later on in their requisite positions.

Figure 5:
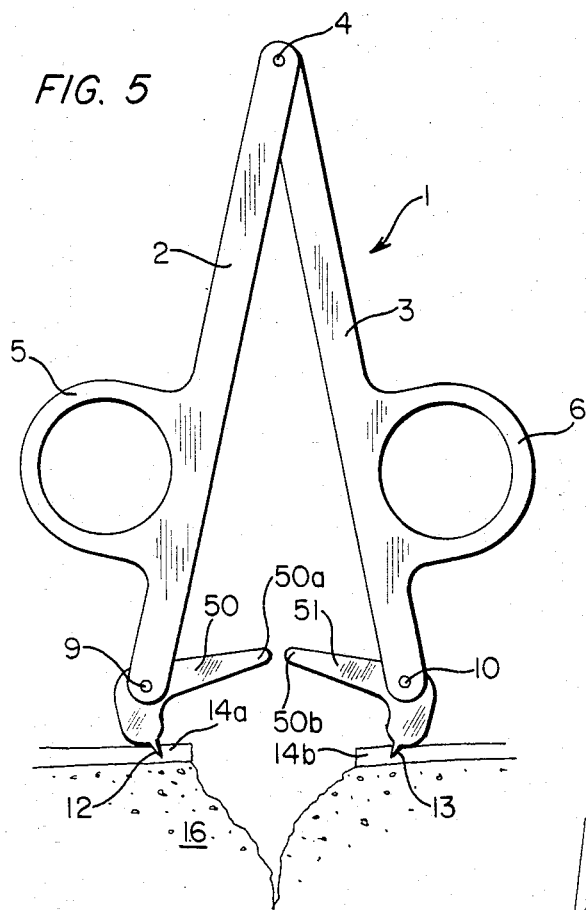
FIG. 5 is a view analogous to FIG. 1 but of a device which represents still a further embodiment of the invention and is shown in its initial position.
Figure 6:
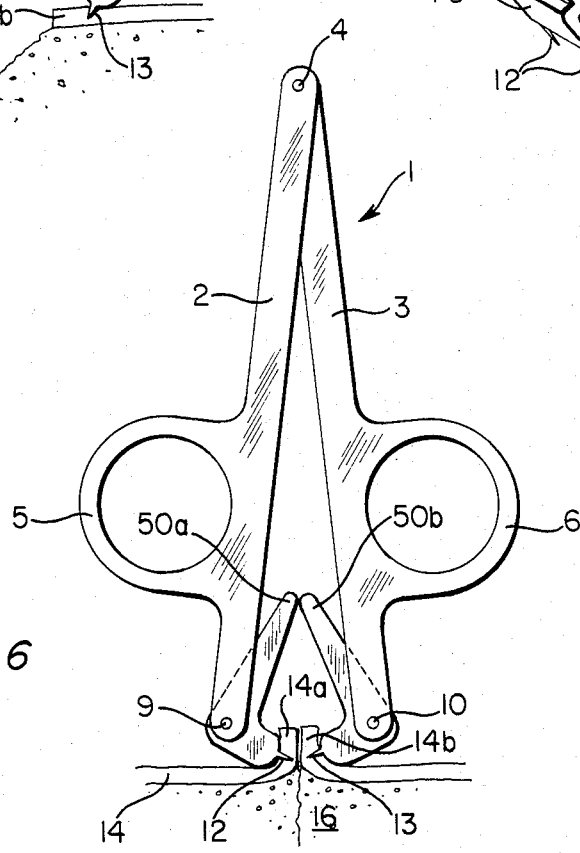
FIG. 6 shows the device of FIG. 5 in its end position.

The embodiment of FIGS. 5 and 6 is quite reminiscent of the one in FIGS. 1–3 and like reference numerals have therefore been used to designate like elements as in FIGS. 1—3.

The structural difference (there is no functional difference) in FIGS. 5 and 6 is that the L-shaped arms 50,51 are not connected with one another. Each arm is hinged to a respective section 2 or 3 at 9 and 10 as in FIGS. 1–3, but the proximal ends 50a, 50b of the longer parts of the arms 50, 51 are not at all connected to each other. They are, however, so positioned (FIG. 5) that when the sections 2, 3 move from the starting position of FIG. 5 towards the end position of FIG. 6, the proximal ends 50a, 50b will contact each other and pivot (roll) on each other until they reach their FIG. 6 end position. In so doing they perform the same skin pulling and everting functions as the equivalent arms in the preceding embodiments.

Figure 7:
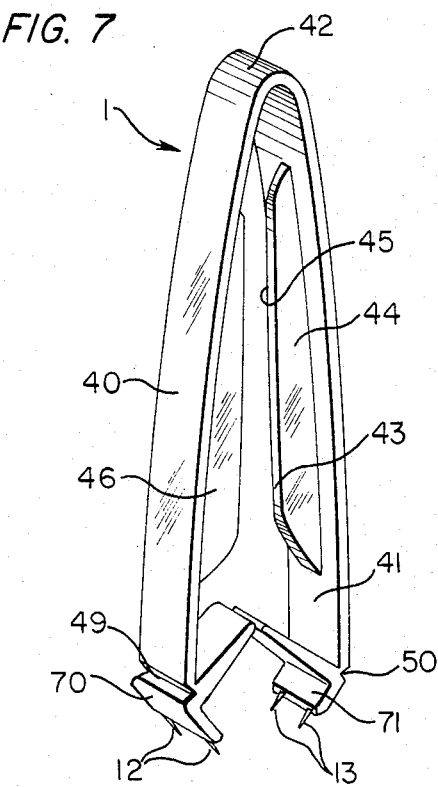
FIG. 7 is a view similar to the one in FIG. 4 but illustrating yet an additional embodiment of the invention.

FIG. 7, finally, illustrates a device 1 similar to the one shown in FIG. 4, from which it differs in the same respect in which FIGS. 5–6 differ from FIGS. 1–3. That is to say that the device 1 in FIG. 7 is a unitary device molded (e.g. injection molded) from synthetic plastic material, the same as in FIG. 4, but that the arms 70 and 71 are not hinged together or otherwise connected to each other at the proximal ends of their longer parts. Just as in FIGS. 5 and 6, these proximal ends will move into engagement with one another when pressure is exerted upon the sections 40, 41 in a sense causing them to move closer together, and they will roll or pivot on each other during this movement, due to the fact that they pivot about the integral hinges 49 and 50.

The function of the embodiment in FIG. 7 is the same as in the preceding embodiments and therefore is not believed to require further discussion.

Any and all embodiments of the invention, i.e. those in FIGS. 1–7 and modifications thereof, may be provided with finger loops (as in FIGS. 1–3 and 5–6) or these loops may be omitted from any and all of the embodiments.

It will be seen from the foregoing that the invention has achieved its intended goal; i.e. that it no longer merely abuts the opposite skin edges in edge-to-edge (or better: edge-surface to edge-surface) contact, but everts the skin edge portions (see FIGS. 2, 3 and 6) so that it is ultimately not the edge-surfaces, but inner skin surface portions extending along the edges, which become abutted.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the inventive contribution to the art. Therefore, such adaptations should—and indeed are intended to—be comprehended within the meaning and scope of equivalence of the appended claims.

I claim:

1. A medical device, particularly a skin approximator, comprising first means for engaging the skin at opposite sides of a wound; second means for drawing the skin together by way of said first means across the wound so as to close the same; third means for everting the edges of the skin by way of said first means before the edges move into a position of mutual abutment in response to operation of said second means, said first means being provided on said second means; means for movably connecting said second means with said third means; and means for facilitating disengagement of said first means from the skin.

2. A medical device as defined in claim 1, wherein said second means comprises a pair of sections which have respective free end portions and are hingeable relative to one another between a starting position in which said end portions are spaced further apart and an end position in which said end portions are closer together.

3. A medical device as defined in claim 1, wherein said first means comprises at least two skin-piercing barbs.

4. A medical device as defined in 1, wherein said third means comprises a pair of arms pivotably connected to said second means and each having a curved endface engageable with the skin at one of the opposite sides of the wound.

5. A medical device as defined in claim 4, wherein said first means comprises at least two skin-piercing barbs each provided on one of said endfaces.

6. A medical device as defined in claim 5, said arms being L-shaped and each having a longer section and a shorter section provided with the respective endface, said longer and shorter sections of each arm being joined with each other at a juncture and the respective pivotable connections defining a pivot axis which passes through said juncture.

7. A medical device as defined in claim 6, said longer sections having respective end portions proximal to each other and each distal from said junction; and means pivotably connecting said end portions to one another.

8. A medical device as defined in claim 6, said barbs being elongated and each having a longitudinal center axis; and said endfaces being curved on a radius which is eccentric relative to said center axis.

9. A medical device as defined in claim 1, said second means comprising a pair of sections having respective free first end portions carrying said third means, said sections being hingeably displaceable relative to one another between a starting position in which said end portions are further apart and an end position in which the end portions are closer together, and said sections further having second end portions distal from said first end portions; and means connecting said second end portions for said hingeable displacement.

10. A medical device as defined in claim 9, wherein the lastmentioned means comprises a pivot connecting said second ends.

11. A medical device as defined in claim 9, wherein the last mentioned means comprises a portion which is unitary with and connects said second ends to one another.

12. A medical device as defined in claim 1, wherein at least some of said means are at least in part of metallic material.

13. A medical device as defined in claim 1, wherein at least some of said means are at least in part of synthetic plastic material.

14. A medical device as defined in claim 1, said second means comprising a pair of elongated sections which are hingeable relative to one another, said facilitating means comprising finger-engaging and positioning means on said sections.

15. A medical device as defined in claim 14, wherein the facilitating means is in form of finger-receiving loops on said sections.

16. A medical device as defined in claim 1, wherein at least said second and third means are unitary with each other in form of a one-piece molded unit of synthetic plastic material.

17. A medical device, particularly a skin approximator, comprising first means for engaging the skin at opposite sides of a wound; second means for drawing the skin together across the wound so as to close the same; and third means for everting the edges of the skin before they move into a position mutual abutment in response to operation of said second means, said third means comprising a pair of L-shaped arms pivotably connected to said second means and each having a curved endface engageable with the skin at the opposite sides of the wound, each of said arms including a longer section and a shorter section provided with the respective endface, said longer and shorter sections of each arm being joined with each other at a juncture and the respective pivotable connections defining a pivot axis which passes through said juncture, said longer sections having respective end portions proximal to each other and each distal from said junction, said end portions being free of connection to one another but engaging each other in pivotal relationship in response to operation of said second means, said first means comprising at least two skin piercing barbs each provided on one of said endfaces.

* * * * *